United States Patent
Hansson et al.

[11] Patent Number: 5,945,296
[45] Date of Patent: Aug. 31, 1999

[54] MONOCLONAL ANTIBODY

[75] Inventors: Yngve Elof Hansson, Enskede, Sweden; Leonor Kremer Baron, Madrid, Spain; Carlos Martínez Alonso, Madrid, Spain; José Mario Mellado Garcia, Madrid, Spain; José Miguel Rodriguez Frade, Madrid, Spain

[73] Assignees: Pharmacia & Upjohn AB, Stockholm, Sweden; Consejo Superior de Investigaciones, Madrid, Spain

[21] Appl. No.: 08/828,300

[22] Filed: Mar. 28, 1997

Related U.S. Application Data

[60] Provisional application No. 60/019,028, May 20, 1996.

[30] Foreign Application Priority Data

Mar. 29, 1996 [SE] Sweden .................................. 9601231

[51] Int. Cl.[6] ........................ G01N 33/53; G01N 33/74; C07K 16/26
[52] U.S. Cl. ........................ 435/7.93; 435/7.1; 435/7.92; 435/7.94; 435/7.95; 435/70.21; 435/172.2; 435/336; 436/518; 436/536; 436/548; 530/388.24; 530/413; 935/104; 935/108; 935/110
[58] Field of Search .................................. 435/7.93, 7.94, 435/7.95, 7.1, 70.21, 172.3, 240.27, 336, 7.92; 436/518, 536, 548; 935/104, 108, 110; 530/388.24, 413; 424/145.1

[56] References Cited

U.S. PATENT DOCUMENTS 5,496,713   3/1996   Honjo et al. ............................ 435/69.4

FOREIGN PATENT DOCUMENTS 63-273496   11/1988   Japan .
WO 90/04788   5/1990   WIPO ............................ G01N 33/53

OTHER PUBLICATIONS

Mazza et al., 1990. Relationship between the antigenic topography and the structure of human growth hormone. Endocrinol. 127: 1002–1008.

Hellstrom et al., 1985. in *Monoclonal Antibodies for Cancer Detection and Therapy* (Baldwin et al., eds), Academic Press, London, p. 20.

Mellado et al., Apr. 1996, Characterization of monoclonal antibodies specific for the human growth hormone 22K and 20K isoforms, J Clin Endocrinol. Metab. 81: 1613–1618.

Cunningham et al, *Science*, 234, 1989.

Hormone Research, Bo Dinesen, vol. 36, No. 1, 1991, 11–16.

Hormone Research, S. Woodhead et al., vol. 36, No. 1, 1991, 17–20.

Journal of Immunoassay, F. Gomez et al., vol. 5, 1984, 145–157.

Mat. Lib. of Medicine, Medline, No. 88228396. Abstract Only.

Mat. Lib. of Medicine, Medline, No. 85213514. Abstract Only.

Mat. Lib. of Medicine, Medline, No. 95157536. Abstract Only.

*Primary Examiner*—James C. Housel
*Assistant Examiner*—James L. Grun
*Attorney, Agent, or Firm*—Pollock, Vande Sande & Amernick

[57] ABSTRACT

The invention relates to monoclonal antibody capable of specific binding to the molecular weight of 20 kDa variant of human growth hormone. This monoclonal antibody has no substantial binding to hGH of molecular weight 22 kDa. The invention also relates to the use of this monoclonal antibody for measurement of hGH 20K, especially in body fluids. The antibodies can be used for detection and quantification of hGH 20K, especially in serum.

10 Claims, 5 Drawing Sheets

MONOCLONAL ANTIBODY

This Application claims the benefit of U.S. Provisional Application No. 60/019,028, filed May 20, 1996.

FIELD OF THE INVENTION

The present invention relates to a monoclonal antibody capable of specifically binding to the 20-kDa molecular weight variant of human growth hormone, referred to herein as hGH 20K. This monoclonal antibody has no substantial binding to hGH having a molecular weight of 22 kDa. The present invention also relates to the use of this monoclonal antibody for measurement of hGH 20K, especially in body fluids. The present invention further relates to use of antibodies for detection and quantification of hGH 20K, especially in serum. Additionally, the present invention relates to a hybriodoma cell line producing the antibody. The cell line has been deposited at DSMZ-Deutsche Sammlung von Mikroorganismen und Zellkulturen GmbH, Braunschweig, Germany, under deposit number DSM ACC 2254 on Feb. 28, 1996.

BACKGROUND OF THE INVENTION

Human growth hormone (hGH) is a 22 kDa molecular weight single chain polypeptide, (hGH 22K), composed of 191 amino acids with two intra-chain disulfide bonds, produced by the anterior pituitary gland (1,2). However, circulating hGH is a complex mixture of different molecular forms, some of which are pituitary-derived, such as hGH 22K and hGH 20K, a human growth hormone 20 kDa molecular weight single chain polypeptide, while others are secreted by the placenta during pregnancy (hGH-V). Furthermore, other tropic hormones, placental lactogen (hPL) and prolactin (PRL), show significant sequence identity with hGH. Other hGH molecular variants derived from post-translational modifications such as deamidation, acylation, glycosylation and oligomerization (3) have also been described. Human growth hormone is coded for by two genes, hGH-N and hGH-V, which are clustered on chromosome 17 together with the highly homologous placental lactogen (hPL) gene (4,5). The main product of the pituitary-expressed hGH-N gene is the 191-amino-acid 22K hGH.

A secondary product of this gene is 20K hGH, derived by alternative mRNA splicing, which lacks 15 residues in the polypeptide chain, from amino acids 32 to 46 (6, 7). This hGH 20K represents 5–10% of pituitary hGH (3), and its biological properties have yet to be defined. While it certainly shares some functions of the 22K isoform, evidence also shows specific activities. Thus, hGH 20K does not bind to hGH receptors in human liver (8) or at least shows decreased binding (9) and has less insulin-like promoting activity (10). The 20K isoform competes with hGH for binding to rabbit mammary gland receptors, indicating that its effect is more like lactogen than somatogen, even though it promotes growth in the hypophysectomized rat (11) see also, for example, European Patent Application EP 587427.

hGH 20K is excreted at a slower rate than hGH and this prolonged persistence of hGH 20K in the circulation may contribute to its higher than expected bioactivity in vivo (Baumann et al, Endocrinology, Vol 117, No 4, 1309–13, 1985).

EP 587 427 disclosed a process for producing hGH 20K by a recombinant method.

Despite the clinical relevance of this peptide hormone family, there is little information on the concentrations of circulating isoforms or the relative contribution of each molecular form of the complex mixture. Selective assays to define hGH 22K and hGH 20K concentrations would be valuable both for diagnostics and basic research (12, 13, 14,). Tools such as monoclonal antibodies (mAb) which specifically block the effect of these proteins could be of great interest in helping to understand their specific biological actions. It has been suggested that the amount and relation between hGH 22K and hGH 20K in circulation could be of importance for special diseases and states of illness, such as diabetes, acromegaly, chronic liver and/or renal disease. A specific and precise method for measuring 20 kDa is thus highly needed.

No method, based on the use of a hGH 20K specific mAb, for specific detection and quantification exists today. Attempts have been done to raise hGH 20K specific mAbs with the purpose of developing immunoassays for hGH 20K, but without success. Reference is made to F Gomez et al, J of Immunoassay, 5 (364), 145–57 (1984). On page 155 of Gomez et al. it is stated "Since the precise pathophysiological relevance of 20K GH is still largely unknown, we felt appropriate to develop an immunoassay for it, obtaining first monoclonal anti hGH 20K antibodies with high specificity. Nevertheless, no stable hybridoma secreting specific anti 20K antibodies could be obtained despite selective immunization of the animals with a highly purified preparation of the variant".

For a long time there has thus been a need for a hGH 20K antibodies with high specificity which could be used in a specific and precise method for measuring hGH 20K. Such an antibody could possibly also be used for therapeutic applications when blocking the biological activity of hGH 20K.

We have now found a solution to the need of the detection and quantification of hGH 20K, as we have generated a mAb specific for hGH 20K. This mAb has been used successfully for the specific detection of this hormone in different types of assays and has also been found to specifically block its biological activity. For that reason it is also useful to study the biological activity of this hormone and analyze its biological significance.

In specific examples we describe the generation and characterization of this mAb. As comparitive antibodies, we also describe monoclonal antibodies specific for hGH 22K and one which recognizes both hGH 20K and hGH 22K.

DETAILED DESCRIPTION OF THE INVENTION

The invention relates to monoclonal antibodies that are specific to human growth hormone (hGH) with a molecular weight 20 kDa (hGH 20K) and have an affinity for hGH 20K of $1 \times 10^8$ $M^{-1}$ or greater, preferably of at least $1 \times 10^9$ $M^{-1}$ and more preferably more than $2 \times 10^9$ $M^{-1}$ as determined by us and described below.

The claimed antibodies are capable of binding to human growth hormone (hGH) with a molecular weight 20 kDa (hGH 20K) with less than 5%, preferably less than 1%, and cross reacting with hGH of molecular weight 22 kDa. The crossreactivity with hGH-V, placental lactogen and prolactin should be small and preferably less than 5%, more preferably less than 1%, as determined in the experimental part as described below.

Also, the following hormones have been tested for cross-reactivity and demonstrate less than 5%, and even less than 1% crossreactivity: Lutenizing hormone (LH), human Chorionic gonadotropin (HCG), Follicle-stimulating hormone (FSH) and Thyroid-stimulating hormone (TSH).

The monoclonal antibody of the present invention can be used for measurement of hGH 20K in, for example body fluids, such as serum, plasma, blood, saliva, urine, lymph fluid etc. The antibody of the invention may be used for immunoassay determination of hGH 20K in samples containing this hormone. The various formats of immunoassay are well known in the art and encompass the steps of:

1) contacting a sample containing hGH 20K with the antibody of the invention so as to form a complex between the antibody and hGH 20K in an amount that is related to the amount of hGH 20K in the sample, and 2) determining the amount of complex formed in a known manner and relating the amount found to the amount of hGH 20K in the sample.

Immunoassays may be heterogeneous or homogenous and competitive or non-competitive (sandwich). The various formats in many cases use labeled immune reagents, in this case hGH 20K or antibody binding to hGH 20K or anti-antibody binding to hGH 20K labeled with enzymes, isotopes, biotin, fluorophores, chromophores etc. (for instance anti-mouse Ig) in order to facilitate the determination of the amount of complex formed.

The antibody of the present invention can be coupled directly to a solid phase or indirectly via another antibody bound to the claimed antibody. The claimed antibody could also be used in a soluble form.

Some formats may make use of precipitation agents, such as anti-antisera and solid phase bound anti-antibodies.

The claimed antibody can be used in a multianalytic assay, for example, for determination of different isoforms of hGH.

The detection of hGH 20K in tissues from different species, for example monkeys, rabbits, dogs, or rats, by immunohistochemical staining is a suggested use for an assay that includes an antibody according to the present invention. The monoclonal antibody according to the present invention can also be used for purification of samples containing hGH 20K.

As hGH 20k has been suggested to have its own therapeutic effect, the present invention also provides a therapeutic composition comprising a therapeutically effective amount of the monoclonal antibody in a pharmaceutically acceptable carrier substance, as well as a method for treating a patient with a need to decrease the amount of 20K by administering the composition.

DEFINITIONS

Body fluids includes, for example serum, plasma, lymph fluid, whole blood, urine, saliva, spinal fluids, tissue culture medium, or cellular extracts. hGH means human growth hormone, hGH 20K means the variant of hGH with a molecular weight of 20 kDa and hGH 22K means the variant of hGH with a molecular weight of 22 kDa.

mAb hGH-33 is a monoclonal antibody capable of binding to human growth hormone (hGH) with a molecular weight of 20 kDa with little cross reacting with a hGH with molecular weight of 22 kDa and which is covered by the claims. mAb hGH-12 is a monoclonal antibody capable of binding to human growth hormone (hGH) with a molecular weight of 20 kDa and with hGH with a molecular weight of 22 kDa, both equally well. mAb hGH-25 and mAb hGH-26 are monoclonal antibodies capable of binding to human growth hormone (hGH) with a molecular weight of 22 kDa without cross reacting with hGH with molecular weight 20 kDa.

By the term antibody (ab) is meant antigen-binding antibody fragments, such as Fv, Fab, Fab2, single chain Fv etc., chimeras, such as class-class and species-species, fused antibodies and recombinant antibodies.

| | |
|---|---|
| BSA | Bovine Serum Albumin |
| cpm | count per minute |
| EIA | enzyme-linked immunoassay |
| FCS | Fetal Calf Serum |
| hGHR | human Growth hormone receptor |
| G-CSFR | Granulocyte Colony Stimulating receptor |
| PBS | phosphate-buffered saline |
| PEG | Polyethylene glycol |

EXPERIMENTAL, MATERIALS AND METHODS

MATERIAL

Recombinant human GH 22K (rhGH-22K Genotropin) and recombinant human GH-variant (rhGH-V) were obtained from Pharmacia Peptide Hormones (Sweden). Purified human GH 20K was kindly donated by professor Paul Roos (Uppsala, Sweden). Purified hPL, hPRL and hGH-22K were from Dr. A. F. Parlow (Pituitary Hormones and Antisera Center, Maryland, USA).

IMMUNIZATION

BALB/c, C57/BL10 and C3H/He mice were immunized subcutaneously with 10–40 µg of protein in 0.1 ml sterile phosphate-buffered saline (PBS) emulsified with Freund's complete adjuvant (Difco Laboratories, USA). Mice were boosted at days 30 and 60 with 20 µg of protein in Freund's incomplete adjuvant, and intraperitoneally in PBS on day 90. Prior to cell fusion, mice were boosted intravenously on days −3 and −2 with 40 µg of hormone in sterile PBS.

Serum from immunized mice was collected 7–10 days after each boost and the presence of specific antibodies was determined in enzyme-linked (EIA) or radioimmunoassays (RIA).

CELL FUSIONS AND PRODUCTION OF MONOCLONAL ANTIBODIES

Cells from spleen and/or lymph nodes of mice were fused with the P3x63Ag8.653 myeloma cell line (CRL 1580, ATCC), using polyethyleneglycol 4000 (Merck, Germany) a fusing agent and following standard protocols (15, 16).

Supernatants were tested for the presence of antibodies by EIA or RIA and positive hybridomas stabilized by limiting dilution using a thymocyte feeder layer, until stable antibody production was achieved. Hybridomas were grown in RPMI-1640, 10% FCS in the absence of antibiotics at 37° C. and 5% $CO_2$.

Monoclonal antibodies were produced both in tissue culture supernatants and in ascites fluids induced with Pristane (Sigma Chemical Co.) -injected mice (17); they were purified by ammonium sulphate precipitation (16) and/or affinity chromatography on immobilized protein-A Sepharose (Pharmacia, Sweden).

The isotype of each mAb was determined in Ouchterlony double-diffusion assays (18) using class and subclass-specific antisera (ICN).

IODINATION AND BIOTINYLATION OF PROTEINS

Hormones (2.5 μg in 20 ml of 50 μM sodium phosphate buffer, pH 7.6) were iodinated using Iodogen-coated tubes (Pierce Chemical Co.) (19) or chloramine-T (20) as oxidizing agents. Iodinated hormones were separated from unincorporated label by gel filtration on a PD-10 Sephadex G25M column (Pharmacia). Specific activity of labeled hormones ranged from 10–50 μCi/μg. Biotinylation was performed as described (21). Hormones and mAb (0.5 mg in 0.5 ml of 150 mM NaCl, 0.1 M carbonate buffer, pH 9) were incubated with 50 μl of 1 mg/ml N-hydroxysuccinimide biotin in dimethyl sulphoxide (Sigma Chemical Co.) for 120 min at room temperature. Uncoupled biotin was removed by dialysis against PBS. Biotin-labeled protein was diluted ½ with glycerol and stored at −20° C.

ENZYME-LINKED IMMUNOASSAYS

Three different enzyme-linked-immunoassays (EIA) were performed, (antibody, antigen and sandwich captures), which varied in their mechanism of antigen presentation to the antibody.

1. ENZYME-LINKED IMMUNOASSAYS—ANTIBODY CAPTURE

Hormones (0.5 μg/ml in PBS, 100 μl/well) were adsorbed to microtiter plates (Maxi-sorb, Nunc) overnight at 4° C. Remaining protein-binding sites were blocked with 0.5% BSA in PBS. After washing plates with distilled water, mAb were incubated for 60 min at 37° C., followed by a peroxidase-labeled goat anti-mouse immunoglobulin antibody (GAM-PO) (Tago, Inc.) and o-phenylenediamine dihydrochloride (OPD, 4 mg/ml in 0.15 M sodium citrate buffer, pH 5.0, Sigma Chemical Co.). The reaction was terminated with 3N sulphuric acid and optical density determined at 492 nm.

2. ENZYME-LINKED IMMUNOASSAYS—ANTIGEN CAPTURE

Monoclonal antibodies were adsorbed to the solid phase, either directly (3 μg/ml in PBS), or via an affinity-purified GAM antibody. After blocking, biotin-labeled hormones diluted 1/500–1/1000 in PBS containing 0.5% BSA were incubated for 60 min at 37° C., followed by peroxidase-labeled streptavidin (Sigma Chemical Co.), for 30 min at 37° C. and OPD. The reaction was terminated as above.

3. ENZYME-LINKED IMMUNOASSAYS—SANDWICH CAPTURE

Purified mAb (3 μg/ml in PBS) were adsorbed onto microtiter plates. After overnight incubation at 4° C. and blocking with 0.5% BSA, hormone dilutions in PBS-0.5% BSA were added and incubated for 60 min at 37° C. After washing, a second biotin-labeled mAb (mAb hGH-12), previously titrated to give optimal binding, was added. The mAb hGH-12 was used as second antibody, as it recognized both molecular forms. After that, peroxidase-labeled streptavidin and OPD were added. The reaction was terminated as before.

RADIOIMMUNOASSAY—SOLID PHASE

Antibodies were adsorbed onto RIA well strips (Costar) via an affinity-purified GAM antibody (2.5 μg/ml in PBS). After blocking with 0.5% BSA in PBS, iodine-labeled hormones were added (20,000 cpm/well) and incubated for 120 min at 37° C. After washing with distilled water, bound radioactivity was counted.

RADIOIMMUNOASSAY—LIQUID PHASE

Antibodies (100 μl/tube), diluted in 10 mM sodium phosphate, 150 mM NaCl, 10 mM EDTA, 0.25% BSA, pH 7.6 (RIA buffer) to give half-maximum binding, were incubated with 30,000 cpm of iodine-labeled hormones in 100 μl of RIA buffer in the presence or absence of unlabeled hormones as competitors. Normal mouse serum was added to give 0.25% in a final reaction volume. After overnight incubation at room temperature, bound and unbound hormone of 400 μl were separated by incubating for 60 min at room temperature with 200 μl of 5% GAM anti-serum and 200 μl of 15% PEG 6000 (Merck), followed by centrifugation at 1520×g for 20 min. Remaining radioactivity in the pellet was counted in a gamma radiation counter.

AFFINITY CONSTANT AND CROSS REACTIVITY DETERMINATIONS

The apparent affinity constants ($K_a$) of the mAb were calculated by Scatchard plot analysis of competitive RIA data (22). Crossreactivities were defined as the amount of competitor required for equal displacement of tracer binding to the mAb.

SDS-PAGE ANALYSIS AND WESTERN BLOTS

Hormones (15 μg of each) were electrophoresed on 15% (w/v) SDS-polyacrylamide gels according to the method of Laemmli (23). Gels were stained with Coomassie Blue or transferred to nitrocellulose on a semi-dry blotter (Bio Rad) for 60 min at 250 mA in a 48 mM Tris base, 39 mM glycine, 20% methanol buffer containing 0.037% SDS. After blocking with 10% non-fat dry milk in PBS, the mAb were incubated with agitation for 120 min at room temperature, followed by a 1/2500 diluted GAM-PO antibody (Tago Inc.). The blot was developed using a 4-chloro-1-naphthol substrate (Sigma Chemical Co.).

CELL PROLIFERATION ASSAY

Ba/F3 cells transfected with the chimeric construct hGHR/G-CSFR were grown in RPMI-1640 media supplemented with IL-3 (10 U/ml) and 10% FCS at 37° C. in 5% $CO_2$. Cells (20×10$^5$ cells/ml) were washed in the same medium without IL-3, and 25 μl of the cell suspension were added to 96-well plates. Cells were treated with various concentrations of hormones (0.001 nM–10 nM) in a final volume of 100 μl for 18 h at 37° C. In competition assays, different concentrations of purified mAb (1–450 nM) and hormones (0.001–10 nM) were preincubated for 18 h at 4° C. before treatment of cells. To measure DNA synthesis, 1 μCi/well of $^3$H-thymidine were added (5 Ci/mmol). After 4 h incubation at 37° C. in 5% $CO_2$, cells were collected and washed on glass filters. Radioactivity was counted with a β counter.

RESULTS

EXAMPLE 1

Analysis of Sera in Antibody Capture EIA

When sera from hGH 20K- or 22K-immunized mice were analyzed in an antibody capture EIA it was found that all mice responded to the corresponding immunogen, with titers (antiserum dilution giving half-maximum binding) of 1/500–1/100,000, depending on the screening assay employed and the immunogen used.

Sera from hGH 20K-immunized mice were analyzed in antibody capture EIA using solid phase-bound hGH 20K and hGH 22K. Titers ranged from 1/500–1/10,000 for both hormones, showing no specificity for hGH 22 or 20K.

EXAMPLE 2

Radioimmunoassay—Solid Phase

After fusion, hybridoma clones were screened by solid phase RIA using $^{125}$I-hGH 20K, and eight hybrids showed binding activity (eight times or more than that of background). Only one antibody did not recognize $^{125}$I-hGH 22K in solid-phase RIA, and it was selected for stabilization and further characterization (hGH-33). The other seven antibodies recognize both hGH 20K and 22K.

EXAMPLE 3

Radioimmunoassay—Liquid Phase

Sera from mice immunized with hGH 22K were analyzed in liquid-phase RIA against the 22K protein. All sera showed high titers for the immunogen (>1/10,000), and mice were subsequently used for cell fusions. After fusions, hybrids producing antibodies which bind $^{125}$I-hGH 22K were selected and stabilized. Two were hGH 22K-specific (mAb hGH-25 and mAb hGH-26), while another (mAb hGH-12) recognized the two molecular forms equally well.

EXAMPLE 4

Antigen-capture EIA and Competitive Liquid-phase RIA

The selected hybrids from Example 2 were tested in antigen-capture EIA using biotin-labeled and unlabeled hormones as competitors, or in a competitive liquid-phase RIA. The binding characteristics of mAb hGH-33 and as controls mAbs the three, hGH-25, hGH-26, and hGH-12, respectively, are summarized in Table I.

Figure 1A:
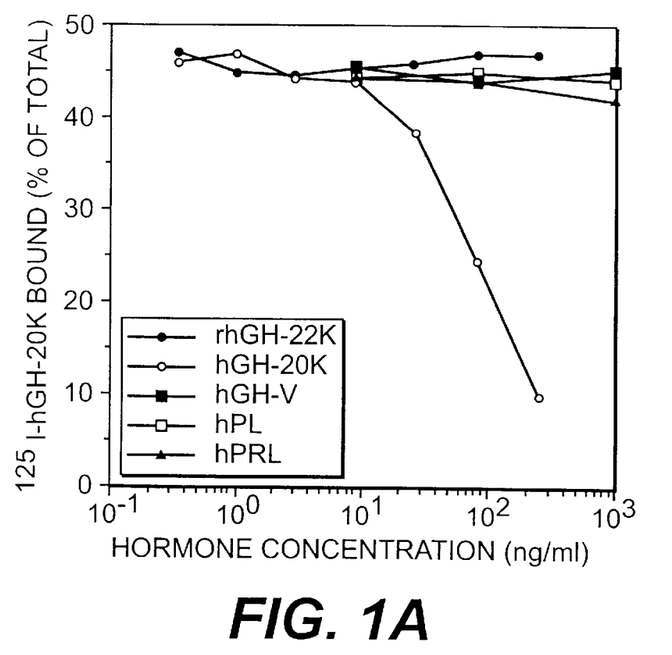
FIGS. 1A–1C represent graphs that illustrate the inhibition of mAb-$^{125}$I-hGH(20K or 22K) binding with unlabeled rhGH-22K, hGH-20K, hGH-V, hPL and hPRL. In particular the Figures correspond to mAb hGH-33 (FIG. 1A), hGH-12(FIG. 1B) and hGH-25 (FIG. 1C).
Figure 1B:
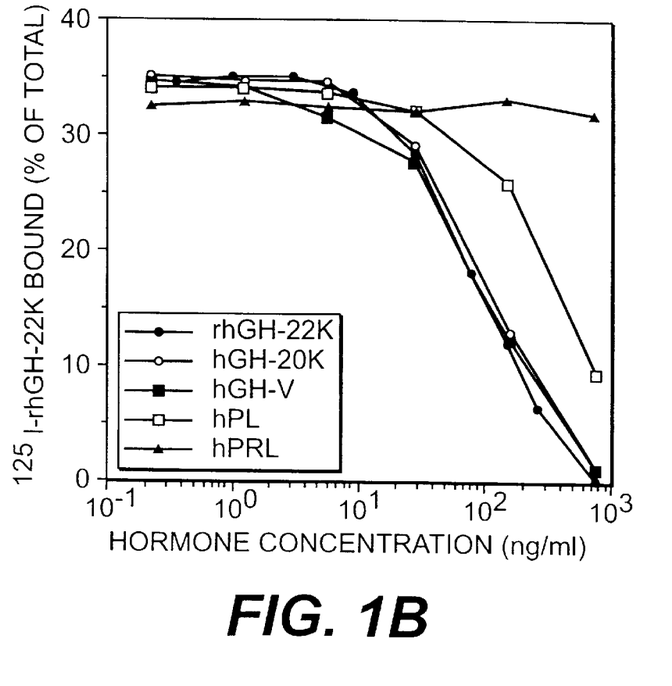
Figure 1C:
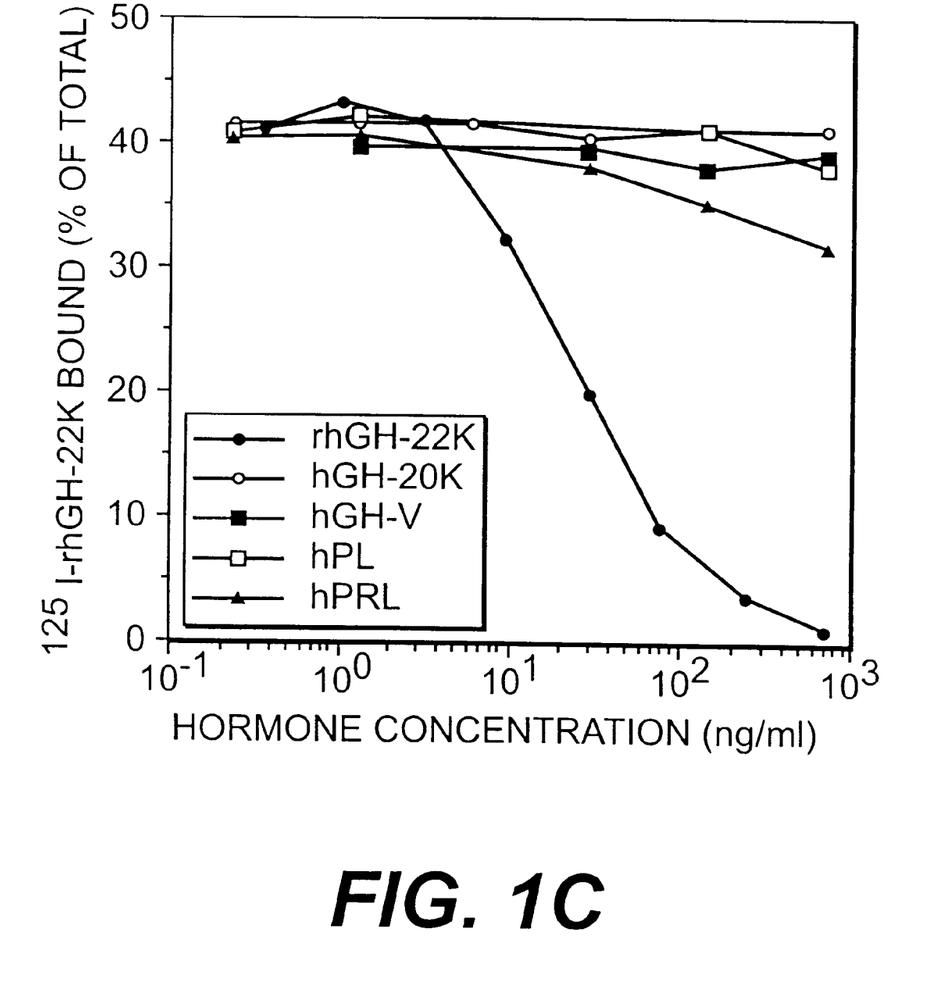

Competitive RIA using iodine-labeled hormones and specific mAb were used for the quantification of the hormones. In FIG. 1 the inhibition of mAb-$^{125}$I-hGH(20K or 22K) binding with unlabeled rhGH-22K, hGH 20K, hGH-V, hPL and HPRL is shown.

FIGS. 1A to 1C correspond to mAb hGH-33 (A), hGH-12(B) and hGH-25 (C). Bound GH is the radioactivity present in the pellet and is expressed as a percentage of total $^{125}$I-hGH applied.

The hGH-25 mAb was employed for hGH 22K, with a detection limit for this isoform of 0.25 nM, while the remaining hormones tested (hGH 20K, hGH-V, hPL and hPRL) did not compete, even at 1,000-fold higher concentrations (FIG. 1C). The hGH-33 mAb was used for hGH 20K, with a detection limit of 0.5 nM, while negligible competition was observed for the rest of the hormones tested (FIG. 1A).

Data from competitive RIA using $^{125}$I-hGH 20K showed that (mAb) hGH-33 has an apparent $K_a$ for hGH 20K of $2.2 \times 10^9$ $M^{-1}$ and less than 1% crossreactivity with hGH 22K, hGH-V, hPL and hPRL (FIG. 1A). The mAb hGH-12 recognizes hGH-V, hGH 20K and hGH 22K equally well, has 40% crossreactivity for hPL and <1% with hPRL (FIG. 1B). The other two mAb (hGH-25 and hGH-26) are hGH 22K-specific, showing negligible crossreactivity with the related hormones and with an apparent $K_a$ of $10^8$–$10^{10}$ $M^{-1}$ (FIG. 1C).

TABLE I

Principal characteristics of the monoclonal antibodies

| monoclonal antibody | $K_a \times 10^9$ $(M^{-1})$[1] | CROSSREACTIVITY (%)[2] | | | | |
|---|---|---|---|---|---|---|
| | | 22K | 20K | hGH-V | hPRL | hPL |
| hGH-25 | 7.5 | 100 | <1 | <1 | 2 | <1 |
| hGH-26 | 3.5 | 100 | <1 | <1 | 5 | <1 |
| hGH-33 | 2.2 | <1 | 100 | <1 | <1 | <1 |
| hGH-12 | 3 | 100 | 80 | 100 | <1 | 40 |

[1] Apparent affinity constants were calculated from competitive RIA with hGH 22K (hGH-25,26 and 12) or hGH 20K (hGH-33) using Scatchard plot analysis. [2] Crossreactivities are expressed as the inverse percentage of the amount of unlabeled hormone required for 50% displacement of labeled hormone from the mAb.

EXAMPLE 5

Antibody Capture EIA

In antibody-capture EIA, the binding characteristics of mAb vary. mAb hGH-33, does not recognize solid phase-adsorbed hormones, while this is not the case for mAbs hGH-12, hGH-25 and hGH-26 (data not shown).

EXAMPLE 6

Sandwich Assay

To test the feasibility of the use of these mAb for specific detection of the various hGH molecular forms, two different sandwich assays have been developed. In each, an isoform-specific mAb is used as capture antibody, hGH-33 in the case of hGH 20K and hGH-26 for hGH 22K. In both assays, biotin-labeled mAb hGH-12 was used as second antibody, as it recognizes both molecular forms.

Figure 2A:
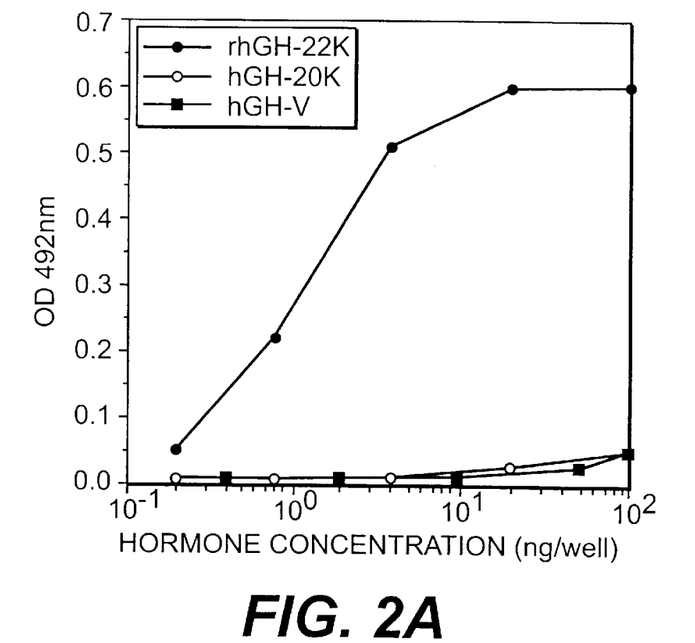
FIGS. 2A and 2B represent graphs that illustrate sandwich capture assays for the specific detection of hGH isoforms. In particular, FIG. 2A relates to hGH-22K and FIG. 2B relates to hGH-20K.
Figure 2B:
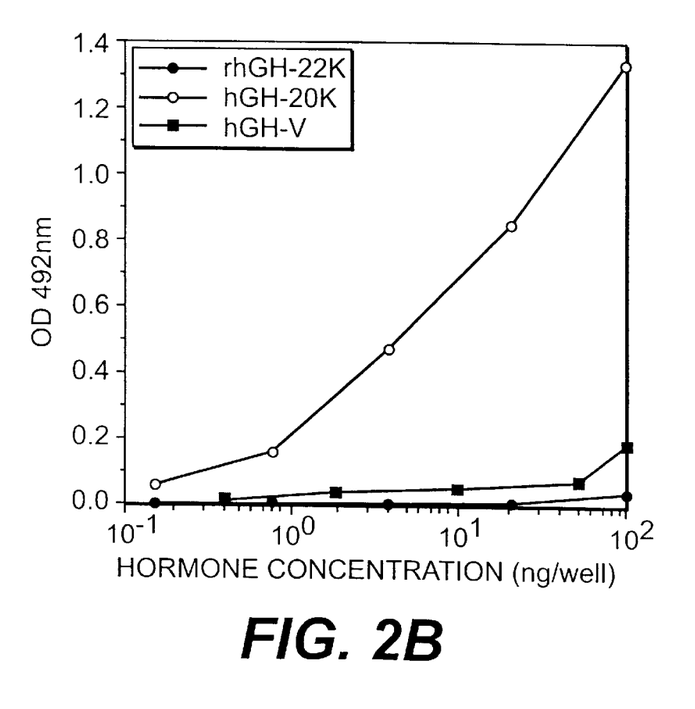

The sensitivity of each specific assay is 0.2 nM for hGH 22K and 0.2 nM for hGH 20K, and no crossreaction with other related hormones was observed (FIGS. 2A and 2B).

EXAMPLE 7

Western Blot

Antibodies hGH-25 and hGH-26 specifically recognized the corresponding purified hormone in western blot, under both reducing and non-reducing conditions. The hGH-33 mAb does not recognize hGH 20K in western blot, as expected from its binding characteristics in antibody capture EIA.

EXAMPLE 8

Cell Proliferation

Antibodies specific for the hGH isoforms were characterized functionally by testing their capacity to block hGHdependent cell growth. Growth stimulation of chimeric hGHR/G-CSF-transfected Ba/F3 cells in response to hGH 22K and hGH 20K. Cells were treated with increasing hormone concentrations for 18 h. DNA synthesis was measured by $^3$H-thymidine incorporation.

Figure 3:
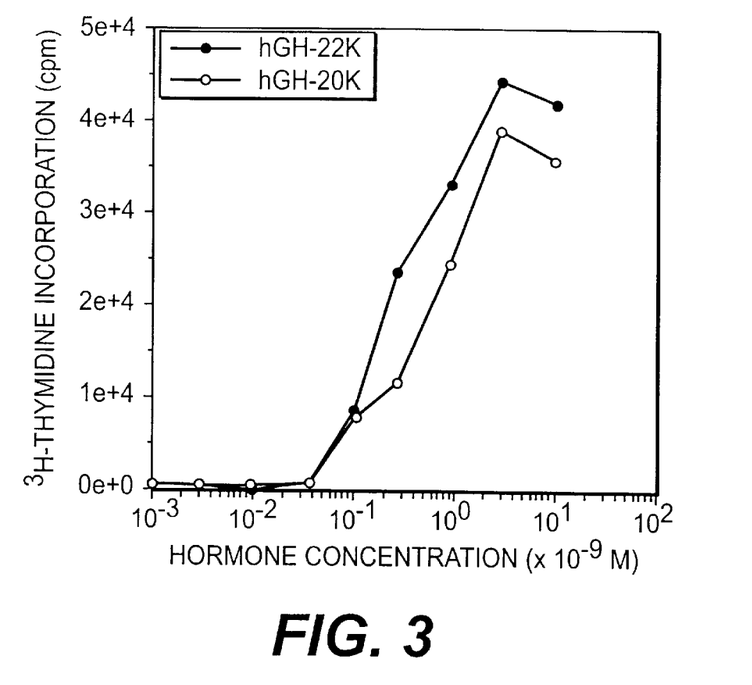
FIG. 3 represents a graph that illustrates growth stimulation of chimeric hGHR/G-CSF-transfected Ba/F3 cells in response to hGH-22K and 20K.

Wild type Ba/F3 cells require exogenous IL-3 to grow in in vitro culture (24). Ba/F3 cells were transfected with a chimeric gene containing the extracytoplasmic domain of the hGH receptor, and the transmembrane and intracytoplasmic domains of the G-CSF (granulocyte colony stimulating factor) receptor. While both wild type and transfected cells grow in the presence of exogenous IL-3, only transfected cells proliferate in the presence of human GH. As shown in FIG. 3, both hGH 20K and 22K promote equal proliferation in the transfected cells. In both cases, the hormone concentration range with maximum effect was 2–10 nM.

Monoclonal antibody blockage of hGH 22K and 20K activity on Ba/F3 transfected cells: Hormones (1 nM) were preincubated with 74 nM hGH-33 and 222 nM hGH-12, 25 and 26 for 18 h at 4° C. before being added to the culture. Data in FIG. 4 represent the mean of triplicate determinations with standard deviation indicated.

Figure 4:
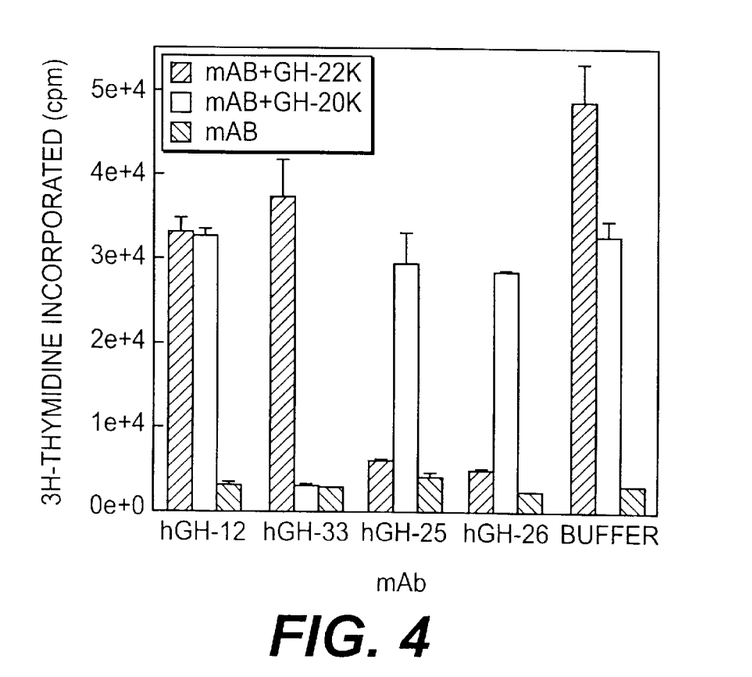
FIG. 4 represents a graph that illustrates monoclonal antibody blockage of hGH 22K and 20K activity on Ba/F3 transfected cells.

The hGH 22K-induced proliferation was specifically inhibited by mAb hGH-25 and hGH-26, but not by hGH-33, whereas the hGH 20K-induced proliferation was only inhibited by hGH-33 (FIG. 4). The hGH-12 mAb, which recognizes both hormones equally well in liquid phase, shows a partial inhibitory effect of hGH 22K and 20K, although this mAb binds and immunoprecipitates the hGH (22 and 20K)-GHBP/GHR complex with high affinity.

EXAMPLE 9

Detection and Quantification of hGH 20K in Serum Samples

As an example of a body fluid, normal human sera was used to investigate the sandwich assay regarding specificity and the usability for quantification of the 20K.

In the assay, the 20K specific antibody, hGH-33 was used as capture antibody and as detection antibody the biotin-labelled hGH-12 was used. For measurements of the signals, time-resolved fluorometry (TRF) was used.

Figure 5:
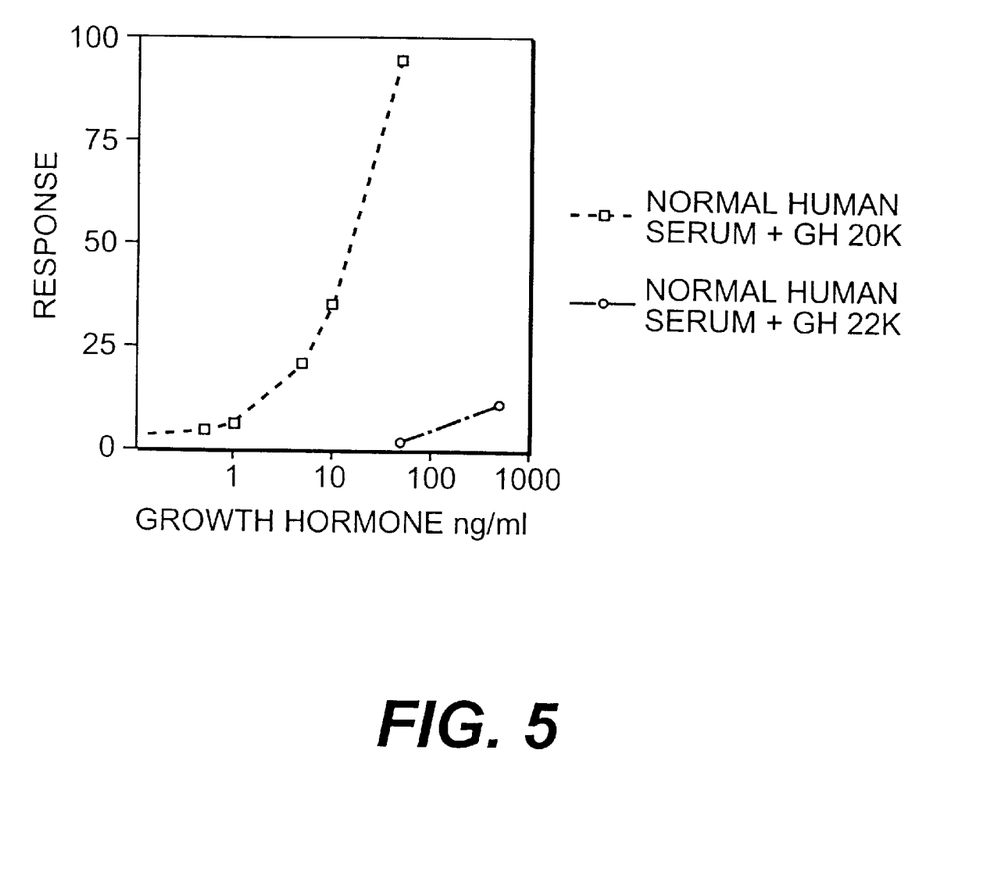
FIG. 5 represents a graph that illustrates dose response of 20K- and 22K hGH added to a human normal serum pool.

A human normal serum pool was used for dose-response testing of hGH 20K and hGH 22K. Increasing concentrations, from 0.5 to 50 ng/ml, of 20K hGH resulted in increasing respons signals. Addition of 50 ng/ml of 22K hGH could not be detected in the assay. Increase of 22K hGH concentration to 500 ng/ml resulted in a weak signal and the crossreactivity was calculated to be less than 0.5% in the 20K sandwich assay (FIG. 5).

The level of sensitivity is below 0.5 ng/ml. In FIG. 5 the dose-response of 20K- and 22K hGH added to a human normal serum pool is shown.

The capture antibody is hGH-33 and the detection antibody is hGH-12 (biotinylated). As testsystem, TR-FIA, Time resolved fluorescent immuno assay was used. This shows clearly that the specific antibody is perfectly working in human normal serum and can thus be used for immunoassay detection and quantification.

DISCUSSION

Growth hormone is present in biological fluids as a mixture of several hGH isoforms in various states of aggregation or in complexes. The net effect of this extraordinarily complex mixture on receptor binding and biological activity is difficult to evaluate with precision. It is likely that many of the hGH forms compete for receptor binding, act as partial agonists and/or antagonists and cross-modulate the bioactivity of the other isoforms (25). This heterogeneity, together with the differences among antibodies (both poly- and monoclonal) used in the assays, may account for the discrepancies observed in hGH determinations (26).

Immunoassays are based on the existence of epitope-specific antibodies. The use of monoclonal antibodies brought an increase in both specificity and sensitivity, as well as in handling of these assays. We have produced and characterized mAb for use as efficient tools to measure hGH isoform concentration precisely and to understand the corresponding biology. Sandwich-type EIA and competitive RIA have been developed to detect each of these variants specifically in buffer systems, with sensitivities comparable to those previously described (12).

The hGH 20K hormone has the same amino acid sequence as hGH 22K, except for an internal deletion of 15 amino acid residues (E32-Q46). Different activities have been claimed for hGH 20K in comparison with hGH 22K (25), such as decreased promotion of insulin-like activity, more lactogenic than somatogenic potency (11) and decreased affinity for hGH receptors as well as for the receptor related-binding protein (8,25). Furthermore, a specific hGH 20K binding protein, non-receptor related, has been described (27, 28, 29). However, most of these data are far from conclusive.

Monoclonal anti-hGH antibodies have been established by several groups (30, 31, 32) and mAb with enhanced responses against hGH 22K in comparison with hGH 20K (33) have been also produced. Here, we have established two hybridomas which secrete mAb specific for hGH 22K, one for hGH 20K and one which recognizes both isoforms equally well. In all cases, the mAb generated have high affinity ($10^8$ M$^{-1}$ to $10^{10}$ M$^{-1}$) and negligible crossreactivity with other related hormones, including hGH-V, hPRL and hPL. The anti-hGH 20K specific antibody was generated using the native protein as immunogen. It probably recognizes a conformational epitope present only in the shorter hGH form, as this mAb does not recognize peptides containing the new E32-Q46 peptide bond (data not shown) and it does not recognize hGH 20K under conditions which might alter its structure (western blot, adsorption to solid phase). In contrast, the two hGH 22K- specific mAb recognize the protein under denaturating conditions. As the only difference between 22K and 20K is the 15 amino acid deletion, hGH-25 and hGH-26 must recognize a sequence within this 15 amino acid stretch.

As the biological activity of hGH 20K and 22K has not yet been clearly differentiated, we tested the effect of these mAb in a GH activity assay, using Ba/F3 cells expressing the hGHR/G-CSFR chimeric receptor and selected for growth with hGH 22K. These cells proliferate equally well in the presence of both 22K and 20K. The hGH-33 mAb specifically blocks the effect of hGH 20K, while hGH-25 and 26 specifically block that of 22K. The sequences described as being involved in hGH 22K receptor binding (34) are also present in hGH 20K. Assuming that similar regions on both hormones are implicated in binding to the receptor, isoform-specific blockage of biological activity using mAb should not be possible, unless these regions present conformational differences. This would allow specific recognition by mAb and could explain the differences in affinity for the hGH receptor between these two hormones (8,25). Further studies on the precise epitopes recognized by these mAb would be of interest for the definition of those hormone structures involved in receptor binding.

In summary, these mAb could be used to quantify hGH 22K and 20K in biological samples, and due to their behavior as specific antagonists, may be of use in the determination of the physiological roles of these isoforms.

We have thus derived and characterized a set of monoclonal antibodies (mAb) specific for the different human growth hormone (hGH) isoforms. These antibodies are named hGH-25, hGH-26, hGH-33 and hGH-12, repectively. The binding characteristics of each antibody to the hGH isoforms (22K and 20K) were analyzed in antibody sandwich, direct and competitive immunoassays, as well as in western blot. hGH-33 is the antibody which is specific against hGH 20K.

One hybridoma cell line, expressing the antibody according to the claims, mAb hGH-33, has been deposited at DSMZ-Deutsche Sammlung von Mikroorganismen und Zellkulturen GmbH, Braunschweig, Germany, under number DSM ACC 2254 on Feb. 28, 1996.

REFERENCES (1) Li CH 1975 The chemistry of pituitary growth hormone: 1967–1973. In: Li CH (ed) Hormonal proteins and peptides. Academic press. New York. vol. 3:1–40.

(2) Lewis U D, Singh RNP, Tutwiler G F, Sigel M B, Vanderlaan E F, Vanderlaan W P 1980 Human growth hormone- a complex of proteins. Rec Prog Horm Res 36:477–504

(3) Baumann G 1990 Growth hormone binding proteins and various forms of growth hormone: implications for measurements. Acta Paediatr Scand (Suppl) 370:72–80

(4) Chen E Y, Liao Y C, Smith D H, Barrera-Saldaña H A, Gelines R F, Seeburg P H 1989 The growth hormone locus: nucleotide sequence, biology and evolution. Genomics 4:479–497

(5) Barsh G S, Seeburg P H, Gelinas R E 1983 The human growth hormone gene family: structure and evolution of the chromosomal locus. Nuc Acid Res 11:3939–3058

(6) Lewis U J, Dunn J T, Bonewald L F, Seavey B K Vanderlaan W P 1978 A naturally occurring structural variant of human growth hormone. J Biol Chem 253:2679–2687

(7) Lewis U J, Bonewald L F, Lewis L J 1980 The 20,000-dalton variant of human growth hormone: location of the amino-acid deletions. Biochem Biophys Res Commun 92:511–516

(8) Mc Carter J, Shaw M A, Winer L A, Baumann G 1990 The 20,000 Da variant of human growth hormone does not bind to growth hormone receptors in human liver. Mol Cell Endocrinol 73:11–14

(9) Wohnlich L, Moore W V 1982 Binding of a variant of human growth hormone to liver plasma membranes. Horm Metab Res 14:138–141

(10) Frigeri L G, Peterson S M, Lewis U J 1979, The 20,000-dalton structural variant of human growth hormone: Lack of some early insulin-like effects. Biochem Biophys Res Commun 91:778–782

(11) Lewis U J 1992 Growth hormone. What is it and what does it do?. Trends Endocrin. Metabol. 3:117–121

(12) Chatelain P, Bouillat B, Cohen R, Sassolas G, Souberbielle J C, Ruitton A, Joly M O, Job J C I 1990 Assay of growth hormone levels in human plasma using commercial kits: analysis of some factors influencing the results. Acta Paediatr Scand (Suppl) 370: 56–61

(13) Woodhead S, Turner G 1991 Accuracy of growth hormone measurements. Horm Res 36 (suppl):17–20

(14) Lewis U J, Sinha Y N, Haro L S 1994 Variant forms of human growth hormone in serum. Acta Paediatr (suppl) 399:29–31

(15) Galfre G, Howe S C, Milstein C, Butcher G W, Howard J C 1977 Antibodies to major histocompatibility antigens produced by hybrid cell lines. Nature 266: 550–552

(16) Harlow E, Lane D. 1988 Antibodies, a laboratory manual. In: Harlow I and Lane D (eds). Cold Spring Harbor Laboratory. New York.

(17) Hoogenraad N J, Wraight C J. 1986 The effect of pristane on ascites tumor formation and monoclonal antibody production. Methods Enzymol 121:375–381

(18) Ouchterlony Ö. 1949 Antigen-antibody reactions in gels. Ark Kemi Mineral Geol 26:1, last page.

(19) Fraker P J, Speck J C 1978 Protein and cell membrane iodinations with a aparingly soluble chloramide, 1,3,4,6-tetrachloro-3a,6a-diphenylglycoluril. Biochem Biophys Res Commun 80:849–857

(20) Hunter W M, Greenwood F C 1962 Preparation of iodine-131 labelled human growth hormone of high specific activity. Nature 194:495–496

(21) Goding J W 1987 Monoclonal antibodies: principles and practice. 2nd ed. Academic Press. London (22) Scatchard G 1949 The attractions of proteins for small molecules and ions. Ann NY Acad Sci 51:660–772

(23) Laemmli E K 1970 Cleavage of structural protins during the assembly of the head of bacteriophage T4. Nature (London) 277:680–685

(24) Palacios R, Steinmetz M 1985 IL-3-dependent mouse clones that express B-220 surface antigen, contains Ig genes in germ-line configuration, and generate B-lymphocytes in vivo. Cell 41:727–734

(25) Baumann G 1991 Metabolism of growth hormone (GH) and different molecular forms of GH in biological fluids. Hor. Res. 36:5–10.

(26) Granada M, SanMartí A, Lucas A, Salinas I, Carrascosa A, Foz M, Audí L 1990. Assay-dependent results of immunoassayable spontaneous 24-hour growth hormone secretion in short children. Acta Pedriatr. Scand. 370:63–70.

(27) Baumann G and Shaw M A 1990 Plasma transport of the 20,000-dalton variant of human growth hormone (20K): evidence for a 20K-specific binding site. J Clin Endocrinol Metab 71:1339–1343

(28) Baumann G, Amburn K and Shaw M A 1988 The circulating growth hormone (GH)-binding protein complex: a major constituent of plasma GH in man. Endocrinol 122:976–984

(29) Baumann G and Shaw M 1990 A second, lower affinity growth hormone-binding protein in human plasma. J Clin Endocrinol Metab 70:680–686

(30) Wallis M and Daniels M 1983 Binding specificity of monoclonal antibodies towards fragments of human growth hormone produced by plasmin digestion. FEBS Letters 159:241–245

(31) Basuyaux B, Paolucci F, Clavies C, Hervaud E, Pau B and Peyrouset A 1987 Production and characterization of monoclonal antibodies to human growth hormone. Hybridoma 6:423–431

(32) Ivanyi J 1982 Study of antigenic structure and inhibition of activity of human growth hormone and chorionic somatomammotropin by monoclonal antibodies. Mol Immunol 19:1611–1618

(33) Nakanishi T, Matsui H and Noguchi H 1989 Monoclonal antibodies which preferently bind to 22K human growth hormone rather than its 20K variant. Endocrinol Japon 36:481–490

(34) Cunningham B C, Jhurani P, Ng P, Wells J A 1989 Receptor and antibody epitopes in human growth hormone identified by homolog-scanning mutagenesis. Science 243:1330–1336

We claim:

1. A monoclonal antibody produced by cells of a cell line deposited under deposit number DSM ACC2254.

2. A hybridoma cell line which produces the monoclonal antibody according to claim 1.

3. A method for measuring human growth hormone having a molecular weight of 20 kDa, the method comprising the steps of:
   contacting a sample with monoclonal antibodies produced by cells of a cell line deposited under deposit number DSM ACC2254; and
   determining an amount of a complex formed between the monoclonal antibodies and 20 kDa human growth hormone contained in the sample.

4. The method according to claim 3, wherein the sample includes at least one bodily fluid.

5. The method according to claim 3, wherein the sample includes at least one bodily fluid selected from the group consisting of blood, serum, plasma, saliva, urine, lymph fluid, whole blood, spinal fluid tissue culture medium, and cellular extracts.

6. The method according to claim 3, further comprising the step of:
   relating the amount of complex formed to an amount of 20 kDa human growth hormone in the sample.

7. The method according to claim 3, wherein the amount of complex formed is determined by at least one method selected from the group consisting of homogeneous, heterogeneous, competitive, and non-competitive immunoassays.

8. A method of purifying a preparation including a 20 kDa form of human growth hormone, the method comprising the steps of:
   contacting the preparation with monoclonal antibodies produced by cells of a cell line deposited under deposit number DSM ACC2254; and
   isolating a complex formed between the monoclonal antibodies and 20 kDa human growth hormone contained in the preparation.

9. A method for immunoassay detection and quantification of a 20 kDa form of human growth hormone, the method comprising the steps of:
   contacting a sample containing an amount of the 20 kDa human growth hormone with monoclonal antibodies produced by cells of a cell line deposited under deposit number DSM ACC2254 thereby resulting in formation of complexes between the monoclonal antibodies and the 20 kDa human growth hormone in an amount that is related to the amount of 20 kDa human growth hormone in the sample;
   determining the amount of the complexes formed; and
   relating the amount of complexes formed to the amount of 20 kDa human growth hormone in the sample.

10. A method for producing monoclonal antibodies produced by cells of a cell line deposited under deposit number DSM ACC2254, the method comprising the steps of:
   culturing a hybridoma cell line that produces the antibodies; and
   recovering the antibodies.

* * * * *